(12) United States Patent
Roessl et al.

(10) Patent No.: US 10,080,533 B2
(45) Date of Patent: Sep. 25, 2018

(54) PHOTON-COUNTING DETECTOR

(71) Applicant: KONINKLIJKE PHILIPS N.V., Eindhoven (NL)

(72) Inventors: Ewald Roessl, Henstedt-Ulzburg (DE); Heiner Daerr, Hamburg (DE); Thomas Koehler, Norderstedt (DE)

(73) Assignee: KONINKLIJKE PHILIPS N.V., EIndhoven (NL)

( * ) Notice: Subject to any disclaimer, the term of this patent is extended or adjusted under 35 U.S.C. 154(b) by 355 days.

(21) Appl. No.: 15/104,024

(22) PCT Filed: Dec. 16, 2014

(86) PCT No.: PCT/IB2014/066961
§ 371 (c)(1),
(2) Date: Jun. 13, 2016

(87) PCT Pub. No.: WO2015/092676
PCT Pub. Date: Jun. 25, 2015

(65) Prior Publication Data
US 2016/0324494 A1 Nov. 10, 2016

Related U.S. Application Data

(60) Provisional application No. 61/917,418, filed on Dec. 18, 2013.

(51) Int. Cl.
*G01T 1/24* (2006.01)
*A61B 6/00* (2006.01)
(Continued)

(52) U.S. Cl.
CPC ............ *A61B 6/4241* (2013.01); *A61B 6/032* (2013.01); *A61B 6/035* (2013.01); *A61B 6/405* (2013.01);
(Continued)

(58) Field of Classification Search
CPC ......... A61B 6/4258; A61B 6/425; A61B 6/56; A61B 6/037; A61B 6/542
See application file for complete search history.

(56) References Cited

U.S. PATENT DOCUMENTS

| 4,091,277 A | 5/1978 | Doblhofer |
| 10,028,364 B2 * | 7/2018 | Tsuji ........................ H05G 1/44 |

FOREIGN PATENT DOCUMENTS

WO   2008072181   6/2008

OTHER PUBLICATIONS

Taguchi, et al., "Vision 20/2Q: Single photon counting x-ray detectors in medical imaging", Medical Physics, AIP, Melville, NY, US, vol. 40, No. 10, Jan. 1, 1901.
(Continued)

*Primary Examiner* — Don Wong (57) ABSTRACT

An imaging system (100) includes a radiation source (110) with a focal spot (204) that emits a beam of x-ray photons that traverses an examination region (106). The imaging system further includes a photon counting detector array (122) that detects a sub-set of the x-ray photons that traverse an examination region. The imaging system further includes a controller (116) that generates and transmits a pause signal, in response to a calculated drop in an intensity of the emitted the beam of x-ray photons below a predetermined intensity level, which causes the photon counting detector array to pause detecting the sub-set of the x-ray photons. The imaging system further includes a counter (136) that counts, for each of a plurality of counting periods, the x-ray photons of the sub-set detected by the photon counting detector array in the corresponding counting period.

20 Claims, 7 Drawing Sheets

(51) Int. Cl.
*A61B 6/03* (2006.01)
*H01J 35/10* (2006.01)
*H05G 1/60* (2006.01)
*H01J 35/06* (2006.01)
*H05G 1/56* (2006.01)

(52) U.S. Cl.
CPC .............. *A61B 6/482* (2013.01); *A61B 6/542* (2013.01); *G01T 1/247* (2013.01); *H01J 35/06* (2013.01); *H01J 35/10* (2013.01); *H05G 1/56* (2013.01); *H05G 1/60* (2013.01); *H01J 2235/086* (2013.01)

(56) References Cited

OTHER PUBLICATIONS

Tapiovaara, et al., "SNR and DQE analysis of broad spectrum X-ray imaging", Physics in Medicine and Biology, Institute of Physics Publishing, Bristol GB, vol. 30, No. 6, Jun. 1, 1985.

* cited by examiner

PHOTON-COUNTING DETECTOR

CROSS REFERENCE TO RELATED APPLICATIONS

This application is the U.S. National Phase application under 35 U.S.C. § 371 of International Application No. PCT/IB2014/066961, filed Dec. 16, 2014, published as WO 2015/092676 on Jun. 25, 2015, which claims the benefit of U.S. Provisional Patent Application No. 61/917,418 filed Dec. 18, 2013. These applications are hereby incorporated by reference herein.

The following generally relates to imaging detectors and more particularly to photon-counting imaging detectors, and is described with particular application to spectral computed tomography (CT).

A computed tomography (CT) scanner generally includes an x-ray tube mounted on a rotatable gantry opposite a detector array across an examination region. The rotatable gantry and hence the x-ray tube rotate around the examination region and a subject therein. The x-ray tube emits radiation that traverses the examination region and the subject. The detector array detects radiation that traverses the examination region and generates a signal data indicative thereof.

The detector array can include integrating and/or photon counting detectors. An integrating detector includes a scintillator optically coupled to a photosensor. The scintillator absorbs x-ray photons and produces light (or infrared) photons, and the photosensor senses the light photons and produces an electrical signal indicative thereof. A photon counting detector includes a direct conversion material such as cadmium telluride (CdTe) or cadmium zinc telluride (CdZnTe), which absorbs x-ray photons and directly produces an electrical signal indicative thereof.

With a photon counting detector, the signal output by the detector array is indicative of an energy of the detected radiation. As such, a photon counting detector can be used to count a number of x-ray photons for one or more different energy ranges. However, photon-counting detectors, unlike integrating detectors, have a non-linear response to changes in an intensity of the incident x-ray radiation. Unfortunately, if these changes are registered within an acquisition (counting) period, there will be an increase in noise in the measured data.

Aspects described herein address the above-referenced problems and others.

The following describes an imaging system in which radiation detection is paused only during a time interval of a counting period in which an intensity of the emitted radiation drops due to the slits in the anode of the x-ray tube and/or modulation of the x-ray tube on and off via a switching grid. Radiation emission and/or detection is paused and resumed based on trigger signal(s) and/or a timer signal, which are calculated based on anode characteristics and/or a pre-determined grid switching pattern.

In one aspect, an imaging system includes a radiation source with a focal spot that emits a beam of x-ray photons that traverses an examination region. The imaging system further includes a photon counting detector array that detects a sub-set of the x-ray photons that traverse an examination region. The imaging system further includes a controller that generates and transmits a pause signal, in response to a calculated drop in an intensity of the emitted beam of x-ray photons below a predetermined intensity level, which causes the photon counting detector array to pause detecting the sub-set of the x-ray photons. The imaging system further includes a counter that counts, for each of a plurality of counting periods, the x-ray photons of the sub-set detected by the photon counting detector array in the corresponding counting period.

In another aspect, a method includes emitting a beam of x-ray photons that traverses an examination region. The method further includes detecting x-ray photons that traverse the examination region in a counting period in response to an intensity of the beam of x-ray photons satisfying a predetermined intensity level. The method further includes pausing detecting the x-ray photons in response to the intensity of the beam of x-ray photons not satisfying the predetermined intensity level. The method further includes counting, for the counting period, a number of the detected photons.

In another aspect, a computed tomography scanner includes an x-ray tube that emits radiation, wherein the x-ray tube includes an anode. The computed tomography scanner further includes a counting detector that detects radiation. The computed tomography scanner further includes a controller that temporarily pauses detection of radiation by the counting detector during a counting period in response to a drop in an intensity of the radiation emitted by the x-ray tube below a pre-determined threshold due to emitted radiation traversing slits in the anode.

The invention may take form in various components and arrangements of components, and in various steps and arrangements of steps. The drawings are only for purposes of illustrating the preferred embodiments and are not to be construed as limiting the invention.

Figure 1:
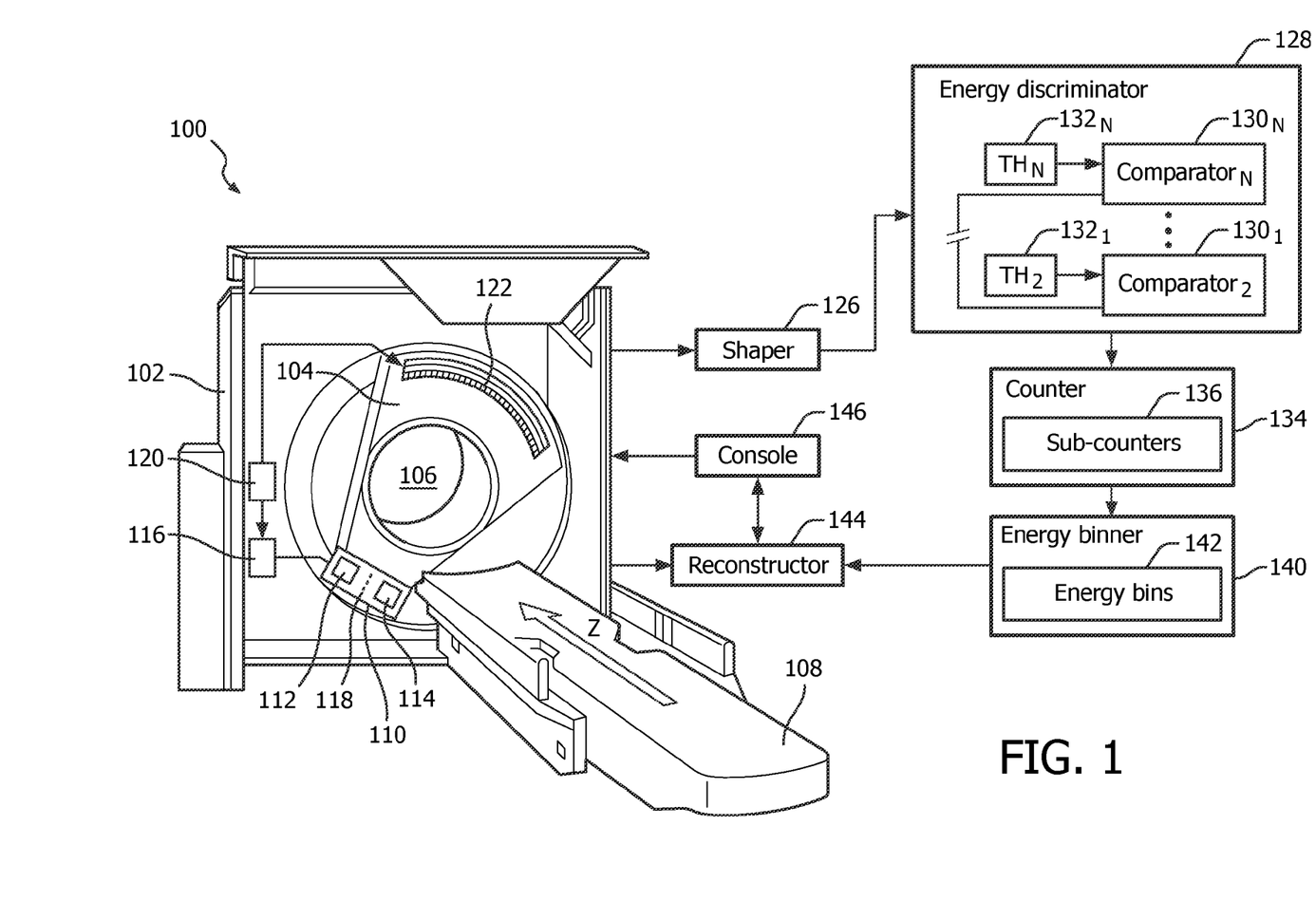
FIG. 1 schematically illustrates an example imaging system including a controller that controls at least one of radiation emission and/or radiation detection.

Initially referring to FIG. 1, an imaging system 100 such as a computed tomography (CT) scanner is schematically illustrated.

The imaging system 100 includes a stationary gantry 102 and a rotating gantry 104, which is rotatably supported by the stationary gantry 102. The rotating gantry 104 rotates around an examination region 106 about a longitudinal or z-axis.

A subject support 108, such as a couch, supports an object or subject in the examination region 106. The subject support 108 can be used to vertically and/or horizontally position the subject or object relative to the imaging system 100 before, during, and/or after scanning.

A radiation source 110, such as an x-ray tube, is supported by and rotates with the rotating gantry 104. The radiation source 110 includes an anode 112 and a cathode 114. A source voltage applied across the anode 112 and the cathode 114 accelerates electrons from the cathode 114 to the anode 112. The electron flow provides a current flow from the cathode 114 to the anode 112, producing radiation that traverses the examination region 106.

Figure 2:
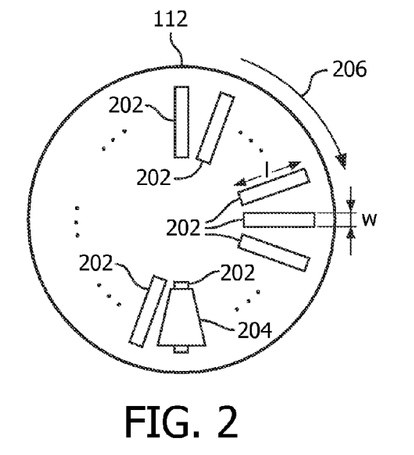
FIG. 2 schematically illustrates an example radiation source anode that includes a plurality of material free regions.

Briefly turning to FIG. 2, a non-limiting example of the anode 112 is schematically illustrated. The anode 112 in FIG. 2 includes a plurality (e.g., 1, 4, 12, 20, 50, etc.) of material free regions 202 such as slits, holes, openings, etc. The illustrated plurality of material free regions 202 have a substantially similar or a same geometry (i.e., rectangular with a length "l" and a width "w"). In a variation, at least one of the plurality of material free regions 202 has a different geometry.

A focal spot 204 corresponds to a target region of the anode 112 for the electrons accelerated from the cathode 114 to the anode 112. The current flow (i.e, the accelerated electrons) interact with the material of the anode 112, producing x-ray radiation, which is emitted therefrom, and heat. It is to be understood that the illustrated geometry of the focal spot 204 is provided for explanatory purposes and is not limiting. Furthermore, the radiation source 110 may include more than one focal spot.

The anode 112 is shown rotating in a first direction 206. However, in another embodiment, the anode 112 may rotate in a direction opposite of the direction 206. As the anode 112 rotates, the plurality of material free regions 202 successively pass through the focal spot 204. As each of the plurality of material free regions 202 passes through the focal spot 204, fewer electrons impinge the anode material (as electrons pass through the material free regions 202), thus less radiation is generated and the radiation of the intensity of the radiation traversing the examiner region 106 decreases.

Figure 3:
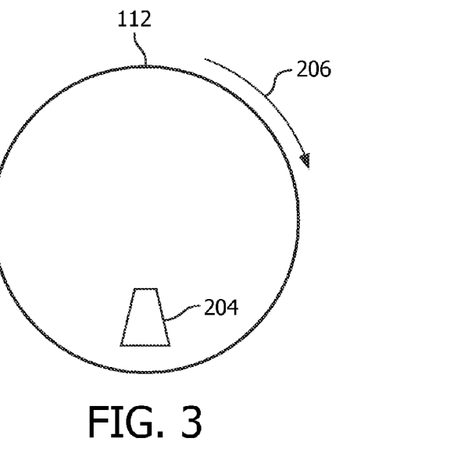
FIG. 3 schematically illustrates an example radiation source anode that does not include any plurality of material free regions.

Turning to FIG. 3, another example of the anode 112 is schematically illustrated. The anode 112 in FIG. 3 is substantially similar to the anode 112 in FIG. 2, except that the anode 112 in FIG. 3 does not include the plurality of material free regions 202 and/or other material free regions. It is to be understood that the example anodes 112 in FIGS. 2 and 3 are provided for explanatory purposes and are not limiting; other anode configurations are also contemplated herein.

Figure 4:
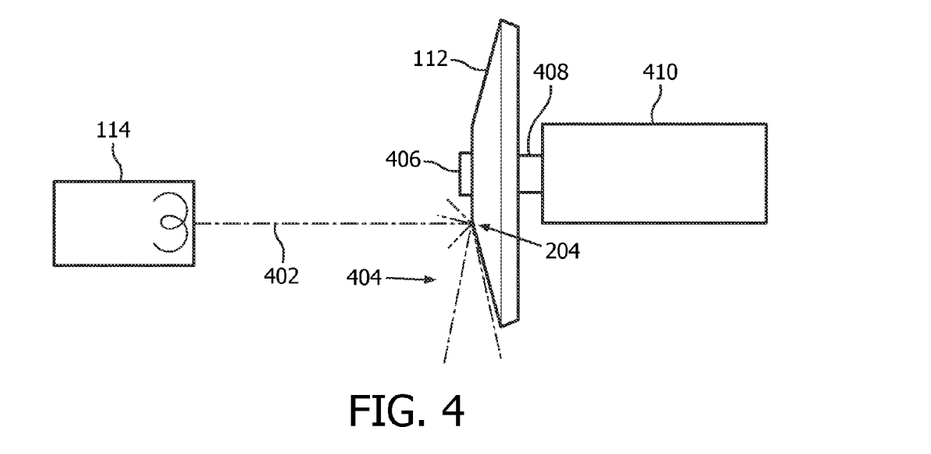
FIG. 4 schematically illustrates an example arrangement of the anode and cathode of the radiation source.

FIG. 4 shows an example arrangement of the anode 112 and the cathode. The illustrated arrangement includes an electron flow 402 from the cathode 114 to the focal spot 204 on the anode 112, and radiation 404 produced in response to an interaction between the electron flow 402 and the material of the anode 112. In this example, the anode 112 is disc shaped and mounted on a spindle 406 carried on a rotary bearing assembly 408 driven by a motor 410. Other anode arrangements are contemplated herein.

Returning to FIG. 1, a grid voltage generator 116 generates a grid voltage for a switching grid 118 between the anode 112 and the cathode 114. The switching grid 118, depending on the grid voltage, allows or inhibits current flow from the cathode 114 to the anode 112. As such, the switching grid 118 can be used to modulate transmission (e.g., turn radiation emission "on" and "off"), etc. In a variation, the grid voltage generator 116 is omitted or not utilized.

A detector array 122 subtends an angular arc opposite the examination region 106 relative to the radiation source 110. The detector array 122 includes a one or two dimensional array of pixels such as direct conversion detector pixels, which include a direct conversion material such as cadmium telluride (CdTe), cadmium zinc telluride (CZT), and/or other direct conversion material. The detector array 122 detects radiation traversing the examination region 106 and generates a signal indicative of an energy thereof.

A controller 120 controls the grid voltage generator 118 and the detector array 122. This includes conveying at least one trigger signal to the grid voltage generator 116 to control the switching grid 118, for example, to turn radiation emission "off" and "on", in instances in which the imaging system 100 also includes the grid voltage generator 116. This also includes conveying the at least one trigger signal to the detector array 122 to turn radiation detection "off" and "on". Temporarily turning radiation emission and detection "off" and "on" during a counting period can be seen as pausing and resuming radiation emission and detection.

As described in greater detail below, in one instance, the controller 120 generates a pause trigger signal that causes the switching grid 118 to inhibit current flow and turn "off" radiation emission and the detector array 122 to turn "off" radiation detection during a time period(s) in which a material free region(s) of the plurality of material free regions 202 passes through the focal spot 204. This mitigates irradiating a subject when radiation is not being detected and/or mitigates detecting radiation during periods in which the detector array is susceptible to undesired count rate drops due to the changes in radiation intensity. A resume, timer signal, etc. can be used to turn radiation emission and detection back "on".

Also described in greater detail below, in connection with the anode 112 of FIG. 3 which does not include the plurality of material free regions 202, the controller 120 generates the pause trigger signal and conveys the pause trigger signal to the detector array 122 to turn "off" radiation detection during a time period(s) in which the switching grid 118 is being used to modulate radiation emission. This mitigates detecting radiation during periods in which the detector array is susceptible to undesired count rate drops due to the changes in radiation intensity during the transitions from radiation emission "on" to "off" and/or "off" to "on". Again, a resume, timer signal, etc. can be used to turn radiation detection back "on".

Also described in greater detail below, where the imaging system does not include or use the grid voltage generator 116, and the controller 120 can still generate the pause trigger signal that causes the detector array 122 to turn "off" radiation detection during a time period in which a material free region of the plurality of material free regions 202 passes through the focal spot 204. This mitigates detecting radiation during periods in which the detector array is susceptible to undesired count rate drops due to the changes in radiation intensity due to the plurality of material free regions 202 of the anode 112. Again, a resume, timer signal, etc. can be used to turn radiation detection back "on".

A pulse shaper 126 receives the signal generated by the detector array 122 and generates a pulse (e.g., a voltage or a current pulse) having a height or amplitude peak that is indicative of the energy of the corresponding incident detected radiation. Optionally, a pre-amplifier can be employed to amplify the signal prior to the pulse shaper 126 generating the pulse. Other pre-processing and/or conditioning can additionally or alternatively be applied to the signal before and/or after pulse shaping.

An energy discriminator 128 includes comparators 130₁, . . . , 130_N (referred to collectively herein as comparators 130) and respective energy thresholds (TH) 132₁, . . . 132_N (referred to collectively herein as thresholds 132), where N is an integer equal to or greater than one. The comparators 130 compare amplitudes (heights) of incoming pulses to the thresholds 132 and generate output signals that indicate which of the thresholds 132 were exceeded by the amplitudes of the pulses, thereby energy-discriminating the incoming pulses based on the thresholds 132.

A counter 134 includes one or more sub-counters 136. The counter 134 increments a count value of at least one of the sub-counters 136 for each threshold based on the output of the energy discriminator 128. For instance, when the output of a comparator for a particular threshold indicates that an amplitude of a pulse exceeds the corresponding threshold, the count value for that threshold is incremented.

An energy binner 140 energy bins the counts based on a plurality of energy bins 142, each bin representing a different energy range. For example, a photon resulting in a count for the lower threshold but not for a next higher threshold, would be assigned to the lower threshold bin.

A reconstructor 144 selectively reconstructs the energy binned signals. This includes reconstructing signals corresponding to a particular energy bin and/or reconstructing the signal across all of the bins, thereby generating non-spectral image data.

A computer serves as an operator console 146. The console 146 includes a human readable output device such as a monitor or display and an input device such as a keyboard and mouse. Software resident on the console 146 allows the operator to interact with the scanner 100 via a graphical user interface (GUI) or otherwise.

Figure 5:
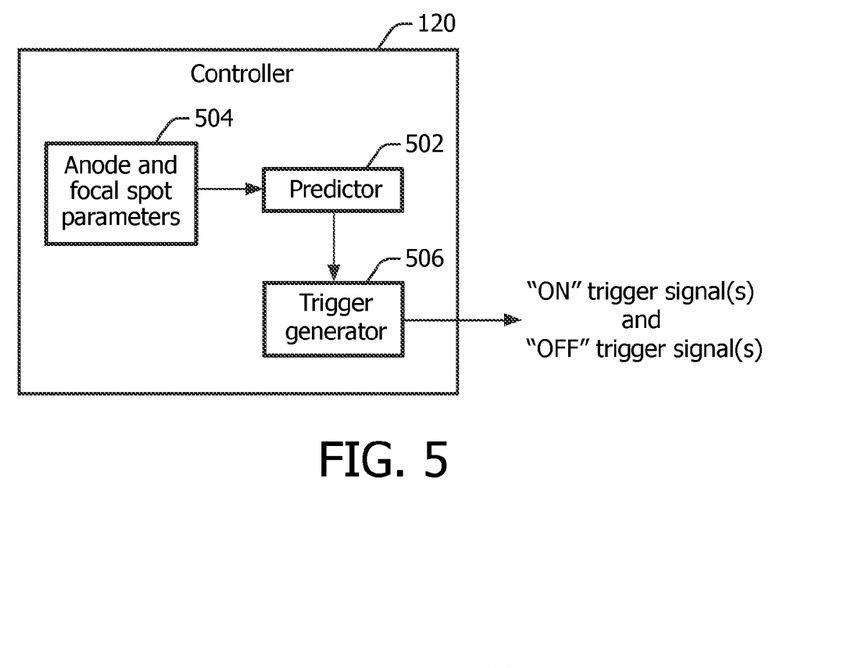
FIG. 5 schematically illustrates an example of the controller, which generates pause and resume trigger signals, in connection with the anode of FIG. 2.
Figure 9:
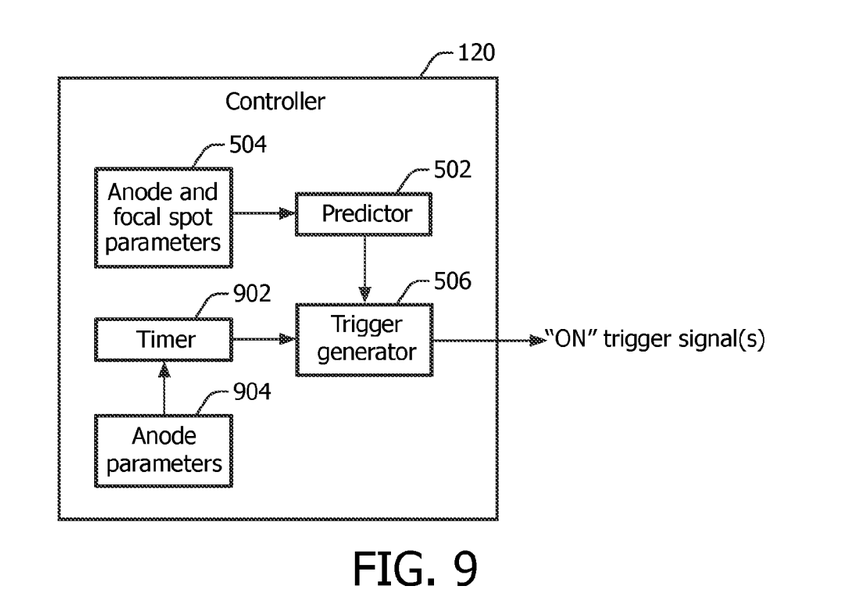
FIG. 9 schematically illustrates an example of the controller, which generates a pause signal and a timer resume time.
Figure 11:
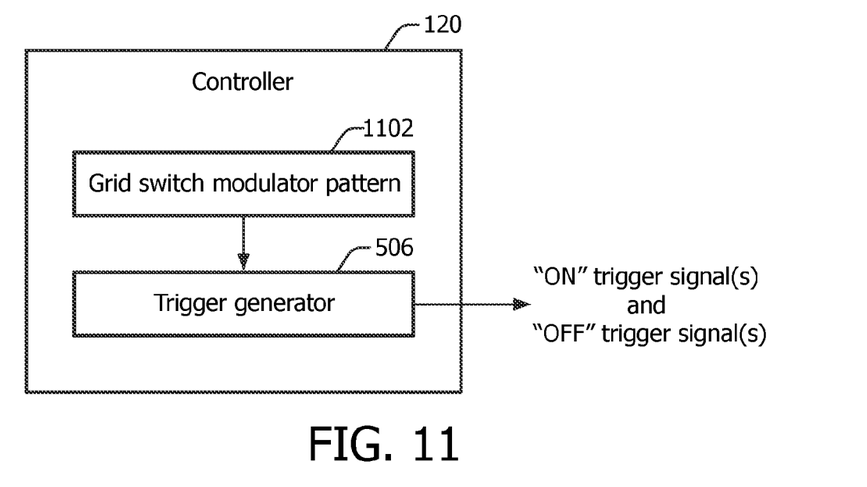
FIG. 11 schematically illustrates an example of the controller in connection with the anode of FIG. 3.

FIGS. 5, 9 and 11 illustrate examples of the controller 120. In FIG. 5, the imaging system 100 includes the grid voltage generator 116 and the anode 112 of FIG. 2. In FIG. 9, the imaging system 100 includes the anode 112 of FIG. 3 and either does not include or does not use the grid voltage generator 116. In FIG. 11, the imaging system 100 includes the grid voltage generator 116 and the anode 112 of FIG. 3, which does not include the plurality of material free regions 202.

Initially referring to FIG. 5, an example of the controller 120 in connection with a configuration in which the imaging system 100 includes the grid voltage generator 116 and the anode 112 of FIG. 3 is illustrated.

In this example, the controller 120 controls the grid voltage generator 116 to turn radiation emission "off" and the detector array 122 to turn data acquisition "off", only during the time periods in which each of the plurality of material free regions 202 traverse the focal spot 204.

The illustrated controller 120 includes a time period predictor 502. The time period predictor 502 calculates a duration of a time period in which each of the plurality of material free regions 202 traverse the focal spot 204 and a time when the time period will occur based on one or more anode and focal spot parameters 504.

In one instance, the time period predictor 502 calculates the time period (calculated time period or "ctp") based on EQUATION 1:

$$ctp = 2\frac{fs\omega}{\omega d}, \qquad \text{EQUATION 1}$$

where "d" represents an anode diameter, "ω" a rotational frequency of the anode 112, and "fsw" represents a width of the focal spot 204. By way of non-limiting example, where d=20-25 cm, ω=150-300 Hz, and fsw=0.6-1.2 mm, the calculated time period is approximately 5-10 microseconds.

The controller 120, based at least on the calculated time period and anode parameters 504 such as "n" and "ω", determines when each time period will occur. In one instance, the time period predictor 502 calculates the time period occurrence (calculated time period occurrence or "ctpo") based on EQUATION 2:

$$ctpo = 2\frac{\pi}{n\omega} \qquad \text{EQUATION 2}$$

where "n" represents a numbers of the material free regions 202 in the anode 112.

The illustrated controller 120 further includes a trigger generator 506. The trigger generator 506, based at least on the calculated time period and calculated time period occurrence, generates at least one pause trigger signal that invokes the grid voltage generator 116 to turn radiation emission "off" and the detector array 122 to turn radiation detection "off". In one instance, the same pause trigger signal invokes both the grid voltage generator 116 and the detector array 122. In another instance, different pause trigger signals invoke the grid voltage generator 116 and the detector array 122.

To turn radiation emission and radiation detection "on", the trigger generator 506, based at least on the calculated time period, generates at least one resume trigger signal that invokes the grid voltage generator 116 to turn radiation emission "on" and the detector array 122 to turn radiation detection "on". Likewise, the same or different resume trigger signals can be used to invoke the grid voltage generator 116 and the detector array 122. In either instance, the resume trigger signal conveyed to the detector array 122 can be time delayed, relative to the resume trigger signal conveyed to the grid voltage generator 116, to allow radiation emission to ramp up before turning radiation detection back "on".

Figure 6:
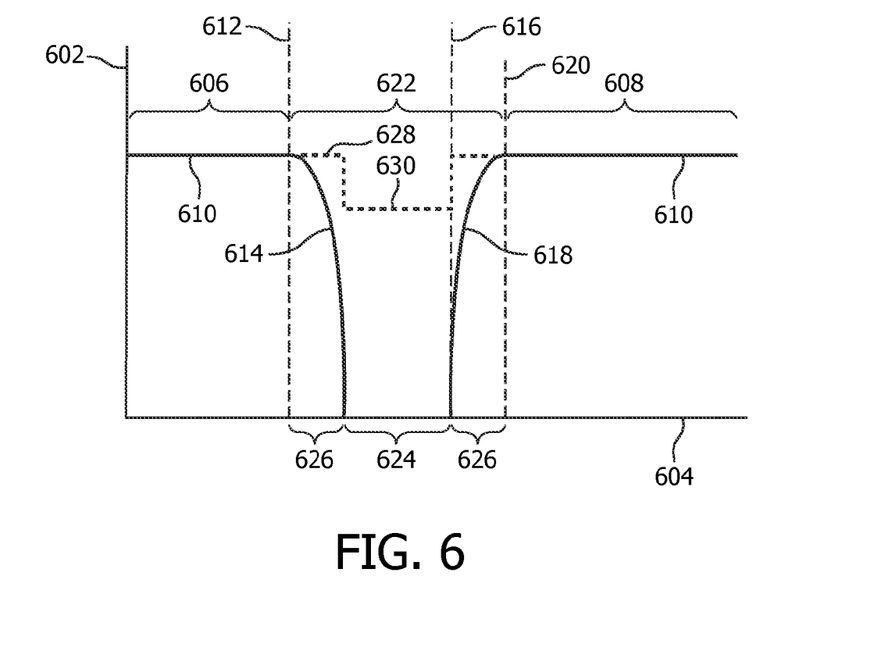
FIG. 6 graphically illustrates control of radiation emission and radiation detection by the controller of FIG. 5, in connection with the anode of FIG. 2.

FIG. 6 graphically illustrates radiation intensity and radiation detection in connection with FIG. 5 in which a single material free region 202 traverses the focal spot 204 during a single acquisition frame or counting period.

In FIG. 6, a first axis 602 represents radiation intensity and a second axis 604 represents a single counting period. Regions 606 and 608 represent regions in which radiation emission and radiation detection are "on". In regions 606 and 608, an intensity value 610 is non-zero. At time point 612, a pause trigger is received by the grid voltage generator 116 and the detector array 122, which turns radiation emission and radiation detection "off". Profile 614 shows the drop in radiation intensity as the radiation emission is transitioning from "on" to "off". Since radiation detection is turned "off" at 612, this transition or drop in radiation intensity is not detected by the detector array 112.

At time point 616, a resume trigger is received by the grid voltage generator 116, and radiation emission is turned back "on". Profile 618 shows the radiation intensity as the radiation emission is transitioning from "off" to "on". Since radiation detection is turned "off", this transition or increase in radiation intensity is not detected by the detector array 112. At 620, the resume trigger is received by the detector array 122, and the detector array 122 begins detecting radiation again. A region 622 represents the region in which radiation detection is turned "off". In region 622, radiation intensity is either zero (sub-region 624) or less than the intensity 610 (sub-regions 626).

In FIG. 6, the time points 612 and 616 are set to avoid the regions 624 and 626 (the finite duration in which the switching of the intensity influences the noise), and the total acquisition frame or counting period includes the regions 616 and 608, with radiation detection turned "off" during the regions 624 and 626. A profile 628 shows a drop 630 in radiation intensity due to a material free region of the plurality of material free regions 202 traversing the focal spot 204, which would occur if the grid voltage generator 116 did not turn radiation emission "off".

The controller 120 can provide a signal that indicates a percentage of the counting period in which radiation detection is turned "on" and/or "off". This can be through a single bit which indicates whether radiation detection was turned "off" and/or "on", or through several bits which provide percentage and/or a time duration in which radiation detection is "off" and/or "on". Where radiation detection is turned "off" over the transition between successive counting periods, in one instance, the counting period can be ended prematurely and/or the beginning of the next counting period can be postponed.

Figure 7:
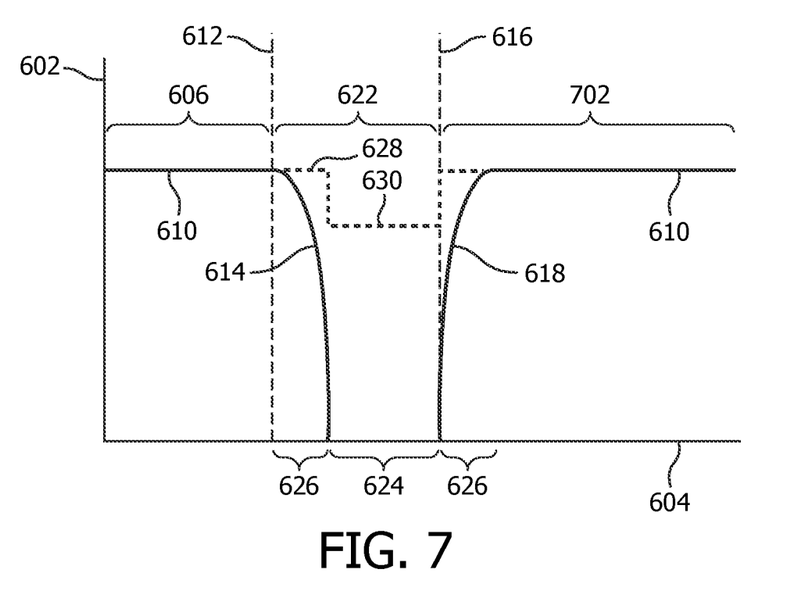
FIG. 7 graphically illustrates different control of radiation emission and radiation detection by the controller of FIG. 5, in connection with the anode of FIG. 2.

FIG. 7 is substantially similar to FIG. 6 except that the resume trigger is received by both the grid voltage generator 116 and the detector array 122 at the time point 616, and the grid voltage generator 116 and the detector array 122 turn "on" radiation emission and radiation detection at the time point 616. In this instance, radiation detection is over a region 702, which includes the region 626 representing the transition from "off" to "on" in which radiation intensity increases.

Figure 8:
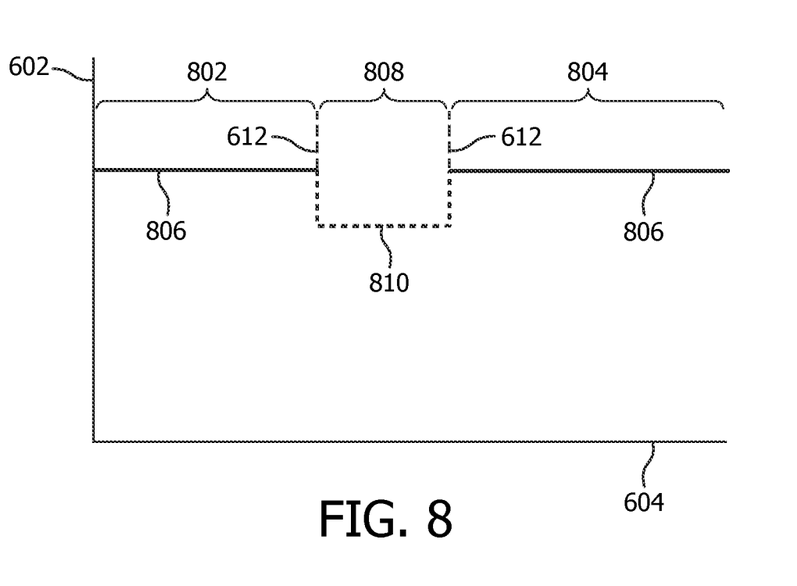
FIG. 8 graphically illustrates control solely of radiation detection by the controller of FIG. 5.

In FIG. 8, either the system 100 does not include the grid voltage generator 116 or the grid voltage generator 116 is not used to turn radiation emission "off" and "on". With this variation, the controller 120 generates the pause and resume trigger signals as discussed in connection with FIG. 5 (e.g., based on the anode and focal spot parameters 504) and/or otherwise. However, the pause and resume trigger signals are only conveyed to the detector array 122 to turn radiation detection "off" and "on". Radiation emission is on and uninterrupted by the trigger signals the entire counting period.

Regions 802 and 804 represent regions in which radiation emission has a pre-determined non-zero intensity value 806. A region 808 represents a region in which the intensity drops to second non-zero intensity value 810, which is less than the pre-determined non-zero intensity value 806. As discussed herein, the region 808 occurs when a material free region 202 traverses the focal spot 204. Radiation detection is turned "off" in the region 808, which mitigates detecting radiation during periods in which the detector array 112 is susceptible to undesired count rate drops due to the changes in radiation intensity due to the material free region 202.

FIG. 9 illustrates a variation of FIG. 5 in which the pause trigger signal is conveyed to the grid voltage generator 116 and the detector array 122 for only a calculated period of time. A timer 902, based at least on the anode parameters 904 such as "n" and "co", calculates the period of time. Upon lapse of the calculated period of time, the timer 902 conveys a signal to the trigger generator 506, which causes the trigger generator 506 to stop conveying the pause trigger signal to the grid voltage generator 116 and the detector array 122 (and/or convey the resume signal to the grid voltage generator 116 and the detector array 122).

Figure 10:
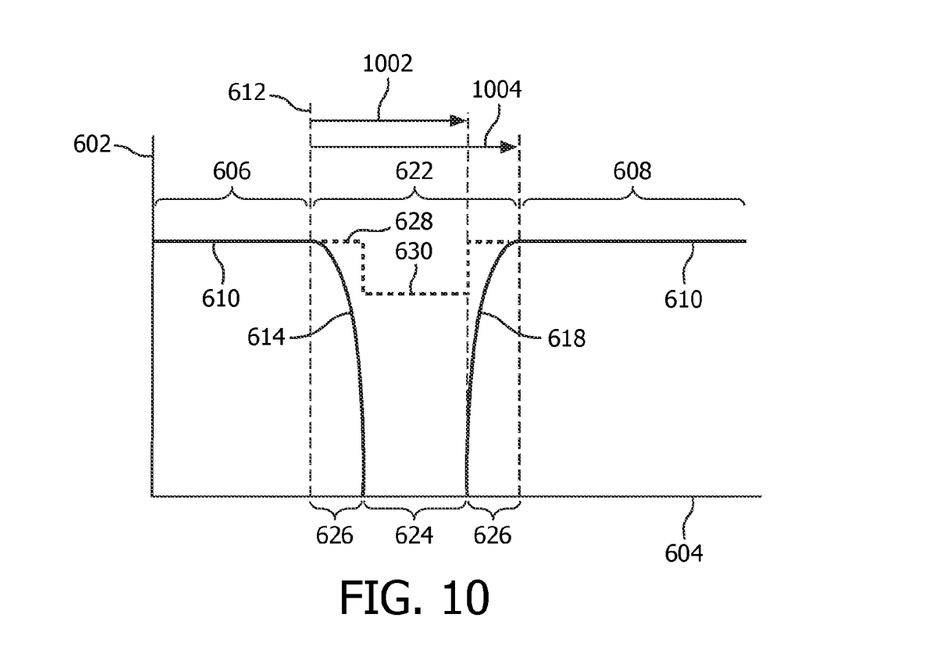
FIG. 10 graphically illustrates control of radiation emission and radiation detection by the controller of FIG. 10.

FIG. 10 graphically illustrates radiation intensity and radiation detection in connection with FIG. 9. This representation is substantially similar to that shown in FIG. 6, except that timer time periods 1002 and 1004, instead of resume triggers, are used to turn radiation emission and radiation detection "on".

In a variation of FIGS. 6, 7 and 10, the grid voltage generator 116 is controlled as described in FIGS. 6, 7 and 10 to turn radiation emission "off" and "on", but the detector array 122 is not turned "off".

FIG. 11 illustrates a variation of FIG. 5 in which the imaging system 100 includes the grid voltage generator 116 and the anode 112 of FIG. 4, which does not include the plurality of material free regions 202. In this variation, the controller 120 includes a grid switch modulation pattern 1102 setting and the trigger generator 506. The trigger generator 506 generates pause and resume trigger signals as discussed in connection with FIGS. 5-7.

However, in this variation, the trigger generator 506 generates the pause and resume trigger signals based on the grid switch modulation pattern 1002 setting. The switch modulation pattern 1002 setting is known in advance and can be obtained from the console 146, the imaging protocol, the radiation source 110, a user input, and/or otherwise. In a variation, the trigger generator 506 generates the pause trigger signal and the timer periods as discussed in connection with FIG. 9.

Other approaches can be utilized to calculate the drops in radiation intensity. For example, in a variation the drop in intensity and triggering is realized by structures on the anode that shift in angle on the anode surface or by making use of the slits themselves, e.g., together with a laser beam and photo-diode combination to detect the arrival of a slit. A trigger signal could then be derived from a level threshold set on the photo-diode output. More triggers could turn "on" the current again, turn "off" radiation detection, and restart counting.

Figure 12:
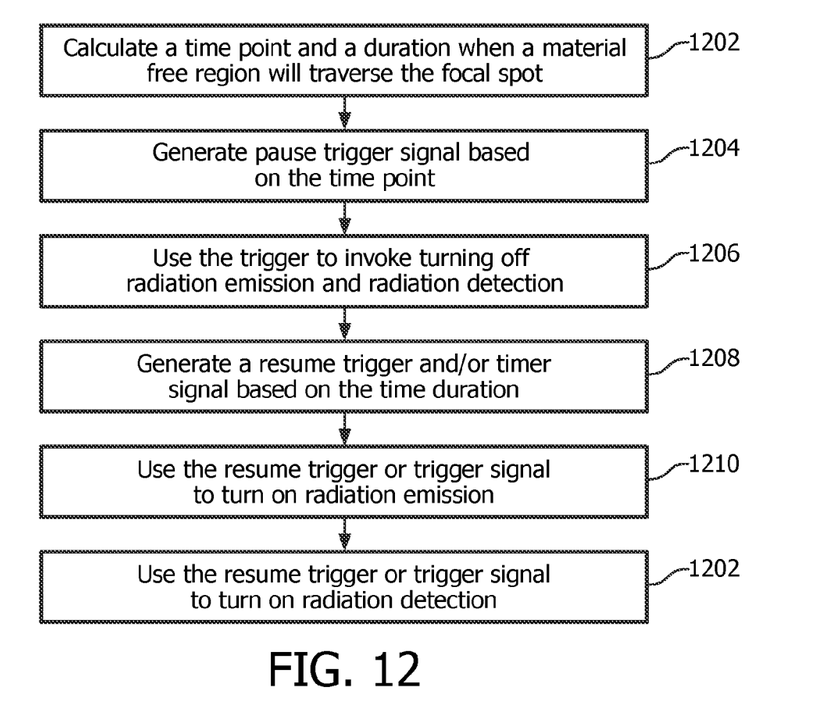
FIG. 12 illustrates an example method in accordance with the embodiments described in connection with FIG. 6, 7 or 10.

FIG. 12 illustrate an example method in accordance with the embodiments described in connection with FIG. 6, 7 or 10.

It is to be appreciated that the ordering of the acts of these methods is not limiting. As such, other orderings are contemplated herein. In addition, one or more acts may be omitted and/or one or more additional acts may be included.

At 1202, a time point and a time duration corresponding to when a material free region 202 will traverse the focal spot 204 for a counting period is calculated.

At 1204, a pause trigger signal is generated based on the time point.

At 1206, the pause trigger signal invokes turning radiation emission "off" and turning radiation detection "off".

At 1208, at least one of a resume trigger signal or a timer signal is generated based on the time duration.

At 1210, the at least one of the resume trigger signal or lapse of the timer signal invokes turning radiation emission "on".

At 1212, the at least one of the resume trigger signal or lapse of the timer signal invokes turning radiation detection "on". Act 1212 can be performed concurrent with act 1210 or subsequent to act 1210 and based on a pre-determined delay.

Figure 13:
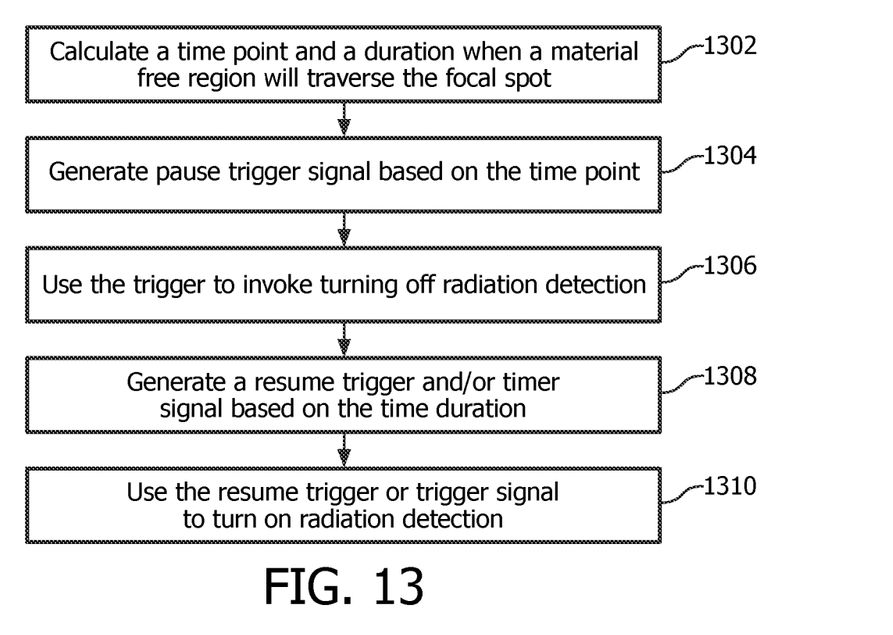
FIG. 13 illustrates an example method in accordance with the embodiments described in connection with FIG. 8.

FIG. 13 illustrate an example method in accordance with the embodiments described in connection with FIG. 8.

It is to be appreciated that the ordering of the acts of these methods is not limiting. As such, other orderings are contemplated herein. In addition, one or more acts may be omitted and/or one or more additional acts may be included.

At 1302, a time point and a time duration corresponding to when a material free region 202 will traverse the focal spot 204 for a counting period is calculated.

At 1304, a pause trigger signal is generated based on the time point.

At 1306, the pause trigger signal invokes turning radiation detection "off". At 1308, at least one of a resume trigger signal or a timer signal is generated based on the time duration.

At 1310, the at least one of the resume trigger signal or lapse of the timer signal invokes turning radiation detection "on".

Figure 14:
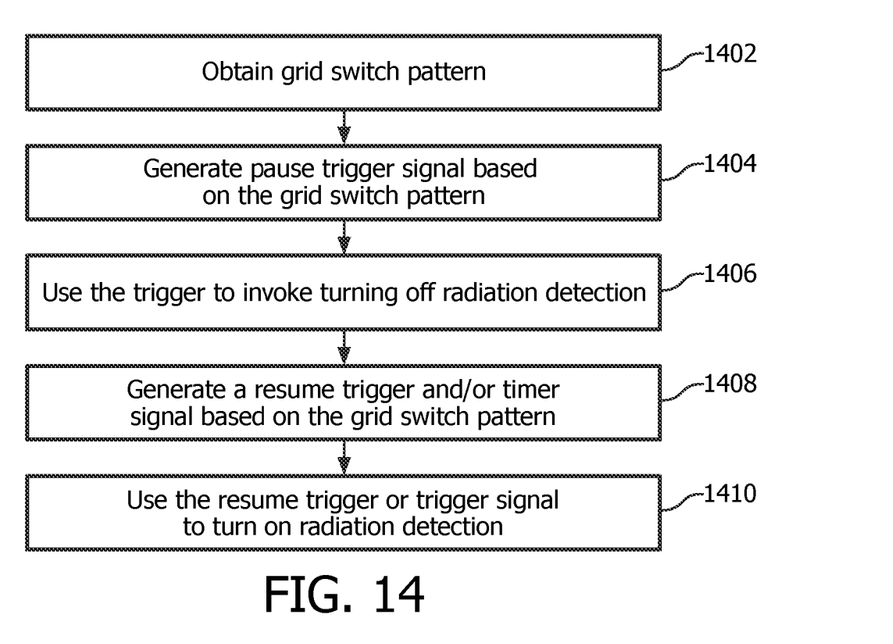
FIG. 14 illustrates an example method in accordance with the embodiments described in connection with FIG. 11.

FIG. 14 illustrate an example method in accordance with the embodiments described in connection with FIG. 11.

It is to be appreciated that the ordering of the acts of these methods is not limiting. As such, other orderings are contemplated herein. In addition, one or more acts may be omitted and/or one or more additional acts may be included.

At 1402, a grid switch pattern is obtained.

At 1404, a pause trigger signal is generated based on the grid switch pattern. At 1406, the pause trigger signal invokes turning radiation detection "off". At 1408, at least one of a resume trigger signal or a timer signal is generated based on the grid switch pattern.

At 1410, the at least one of the resume trigger signal or lapse of the timer signal invokes turning radiation detection "on".

The above acts may be implemented by way of computer readable instructions, encoded or embedded on computer readable storage medium (i.e., physical memory and other non-transitory medium), which, when executed by a microprocessor(s), cause the processor(s) to carry out the described acts. Additionally or alternatively, at least one of the computer readable instructions is carried by a signal, carrier wave and other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An imaging system, comprising:
a radiation source with a focal spot that emits a beam of x-ray photons that traverses an examination region;
a photon counting detector array that detects a sub-set of the x-ray photons that traverse an examination region;
a controller that generates and transmits a pause signal, in response to a calculated drop in an intensity of the emitted the beam of x-ray photons below a predetermined intensity level, which causes the photon counting detector array to pause detecting the sub-set of the x-ray photons; and
a counter that counts, for each of a plurality of counting periods, the x-ray photons of the sub-set detected by the photon counting detector array in the corresponding counting period.

2. The imaging system of claim 1, wherein the controller generates a resume signal in response to a calculated increase in the intensity of the beam of x-ray photons above the predetermined intensity level, and the photon counting detector array resumes detecting the beam of x-ray photons in response to resume signal.

3. The imaging system of claim 1, the radiation source, comprising:
an anode configured to rotate and including a plurality of material free regions; and
a cathode,
wherein the anode rotates thereby rotating the plurality of material free regions which successively rotate through the focal spot.

4. The imaging system of claim 3, wherein the intensity of the emitted radiation drops below the predetermined intensity level in response to a material free region of the plurality of material free regions rotating through the focal spot, and the intensity of the emitted radiation increases above the predetermined intensity level in response to the material free region of the plurality of material free regions being outside of the focal spot.

5. The imaging system of claim 3, further comprising:
a predictor that calculates the drop in the intensity based at least in part on a diameter of the anode, an angular frequency of the anode, a number of the material free regions in the anode, and a width of each of the material free regions in the anode.

6. The imaging system of claim 5, wherein the predictor calculates the increase in the intensity based at least in part on the pause signal, the angular frequency of the anode, and the width of each of the material free regions in the anode.

7. The imaging system of claim 5, the imaging system, further comprising:
a grid switch generator,
wherein the grid switch generator, in response to the pause signal, applies a grid switch voltage between the anode and the cathode, which inhibits electron flow there between, thereby pausing radiation emission.

8. The imaging system of claim 7, wherein the grid switch generator, in response to the resume signal, removes the grid switch voltage, which allows electron flow there between, thereby resuming radiation emission.

9. The imaging system of claim 2, wherein the resume signal includes one of a trigger signal or a timer duration.

10. The imaging system of claim 1, the radiation source, comprising:
an anode; and
a cathode, and the imaging system, further comprising:
a grid switch generator,
wherein the grid switch generator, in response to the pause signal, applies a grid switch voltage between the anode and the cathode, which inhibits electron flow there between, thereby pausing radiation emission.

11. The imaging system of claim 10, wherein the grid switch generator, in response to the resume signal, removes the grid switch voltage, which allows electron flow there between, thereby resuming radiation emission.

12. The imaging system of claim 10, wherein the resume signal includes one of a trigger signal or a timer duration.

13. The imaging system of claim 10, further comprising:
a predictor that calculates the drop and the increase in the intensity based at least in part on a pre-determined grid switch modulation pattern.

14. The imaging system of claim 1, wherein the controller, for each counting period, sets one or more bits that indicate detecting the sub-set of the x-ray photons was paused.

15. A method, comprising:
   emitting a beam of x-ray photons that traverses an examination region;
   detecting x-ray photons that traverse the examination region in a counting period in response to an intensity of the beam of x-ray photons satisfying a predetermined intensity level;
   pausing detecting the x-ray photons in response to the intensity of the beam of x-ray photons not satisfying the predetermined intensity level; and
   counting, for the counting period, a number of the detected photons.

16. The method of claim 15, further comprising:
   calculating when the intensity of the beam of x-ray photons will not satisfy the predetermined intensity level and generating a first calculated signal, wherein the calculation is based at least in part on a diameter of the anode, an angular frequency of the anode, a number of the material free regions in the anode, and a width of each of the material free regions in the anode.

17. The method of claim 15, further comprising:
   pausing emission of the beam of x-ray photons based on the first calculated signal.

18. The method of claim 16, further comprising:
   calculating when the intensity of the beam of x-ray photons will satisfy the predetermined intensity level and generating a first calculated signal, wherein the calculation is based at least in part on the pause signal, the angular frequency of the anode, and the width of each of the material free regions in the anode.

19. The method of claim 16, further comprising:
   resuming emission of the beam of x-ray photons based on the second calculated signal.

20. A computed tomography scanner, comprising:
   an x-ray tube that emits radiation, wherein the x-ray tube includes an anode;
   a counting detector that detects radiation; and
   a controller that temporarily pauses detection of radiation by the counting detector during a counting period in response to a drop in an intensity of the radiation emitted by the x-ray tube below a pre-determined threshold due to emitted radiation traversing slits in the anode.

* * * * *